US00PP19327P2

(12) United States Plant Patent
Kerley et al.

(10) Patent No.: US PP19,327 P2
(45) Date of Patent: Oct. 14, 2008

(54) ***PETUNIA* PLANT NAMED 'KERPRILCOMP'**

(50) Latin Name: *Petunia×hybrida*
Varietal Denomination: Kerprilcomp

(76) Inventors: David W. Kerley, Bethany, 49 Station Road, Over, Cambridge CB24 5NJ (GB); Priscilla G. Kerley, Bethany, 49 Station Road, Over, Cambridge CB24 5NJ (GB)

( * ) Notice: Subject to any disclaimer, the term of this patent is extended or adjusted under 35 U.S.C. 154(b) by 0 days.

(21) Appl. No.: 11/978,132

(22) Filed: Oct. 25, 2007

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L Bell
(74) *Attorney, Agent, or Firm*—C. A. Whealy

(57) ABSTRACT

A new and distinct cultivar of *Petunia* plant named 'Kerprilcomp', characterized by its compact and outwardly spreading to trailing growth habit; freely branching habit; freely flowering habit; double purple violet-colored flowers with darker purple venation; and good garden performance.

2 Drawing Sheets

Botanical designation: *Petunia×hybrida.*
Cultivar denomination: 'Kerprilcomp'.

BACKGROUND OF THE INVENTION

The present invention relates to a new and distinct cultivar of *Petunia,* botanically known as *Petunia×hybrida* and hereinafter referred to by the name 'Kerprilcomp'.

The new *Petunia* is a product of a planned breeding program conducted by the Inventors in Over, Cambridge, United Kingdom. The objective of the breeding program is to create new *Petunia* cultivars with double and attractive flowers.

The new *Petunia* originated from a cross-pollination made by the Inventors on Aug. 15, 2001 in Over, Cambridge, United Kingdom of a proprietary selection of *Petunia×hybrida* identified as code number 01-45-14, not patented, as the female, or seed, parent with a proprietary selection of *Petunia×hybrida* identified as code number 01-45-8, not patented, as the male, or pollen, parent. The new *Petunia* was discovered and selected by the Inventors as a single flowering plant within the progeny of the stated cross-pollination in a controlled environment in Over, Cambridge, United Kingdom on May 30, 2002.

Asexual reproduction of the new *Petunia* by terminal cuttings in a controlled environment in Over, Cambridge, United Kingdom since October, 2002, has shown that the unique features of this new *Petunia* are stable and reproduced true to type in successive generations.

SUMMARY OF THE INVENTION

The cultivar Kerprilcomp has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Kerprilcomp'. These characteristics in combination distinguish 'Kerprilcomp' as a new and distinct cultivar of *Petunia:*

1. Compact and outwardly spreading to trailing growth habit.
2. Freely branching habit.
3. Freely flowering habit.
4. Double purple violet-colored flowers with darker purple venation.
5. Good garden performance.

Plants of the new *Petunia* can be compared to plants of the female parent selection. Plants of the new *Petunia* differ from plants of the female parent selection in the following characteristics:

1. Plants of the new *Petunia* are more trailing than and not as upright as plants of the female parent selection.
2. Plants of the new *Petunia* have double flowers whereas plants of the female parent selection have single flowers.
3. Plants of the new *Petunia* and the female parent selection differ in flower color.

Plants of the new *Petunia* can be compared to plants of the male parent selection. Plants of the new *Petunia* differ primarily from plants of the male parent selection in the flower color as plants of the male parent selection have magenta-colored flowers.

Plants of the new *Petunia* can also be compared to plants of the *Petunia* cultivar Kerpril, disclosed in U.S. Plant patent application Ser. No. 09/399,874 (not abandoned). In side-by-side comparisons conducted in Over, Cambridge, United Kingdom, plants of the new *Petunia* differed from plants of the cultivar Kerpril in the following characteristics:

1. Plants of the new *Petunia* were more compact than plants of the cultivar Kerpril.
2. Plants of the new *Petunia* flowered about three days earlier than plants of the cultivar Kerpril.
3. Plants of the new *Petunia* had darker colored flowers than plants of the cultivar Kerpril.
4. Plants of the new *Petunia* had longer peduncles than plants of the cultivar Kerpril.

BRIEF DESCRIPTION OF THE PHOTOGRAPHS

The accompanying colored photographs illustrate the overall appearance of the new *Petunia,* showing the colors as true as it is reasonably possible to obtain in colored reproductions of this type. Colors in the photographs may differ slightly from the color values cited in the detailed botanically description which accurately describe the colors of the new *Petunia*.

The photograph on the first sheet comprises a side perspective view of a typical plant of 'Kerprilcomp' grown in a hanging basket container.

The photograph on the second sheet is a close-up view of a typical flower of 'Kerprilcomp'.

DETAILED BOTANICAL DESCRIPTION

The photograph and following observations, measurements and values describe plants grown in Over, Cambridge, United Kingdom, under commercial practice during the summer in a glass-covered greenhouse with day temperatures ranging from 18° C. to 28° C., night temperatures ranging from 14° C. to 20° C. and light levels averaging 50 kilolux. Rooted young plants and been growing for about ten weeks when the photographs and description were taken. Plants were pinched one time before planting. In the following description, color references are made to The Royal Horticultural Society Colour Chart, 1995 Edition, except where general terms of ordinary dictionary significance are used.

Botanical classification: *Petunia×hybrida* cultivar Kerprilcomp.

Parentage:

*Female, or seed, parent.*—Proprietary selection of *Petunia×hybrida* identified as code number 01-45-14, not patented.

*Male, or pollen, parent.*—Proprietary selection of *Petunia×hybrida* identified as code number 01-45-8, not patented.

Propagation:

*Type.*—By terminal cuttings.

*Time to initiate roots, summer.*—About ten days at temperatures of 21° C.

*Time to initiate roots, winter.*—About two weeks at temperatures of 21° C.

*Time to produce a rooted young plant, summer.*—About 30 days at temperatures of 20° C.

*Time to produce a rooted young plant, winter.*—About 45 days at temperatures of 20° C.

*Root description.*—Fine, fibrous; white in color.

*Rooting habit.*—Freely branching; dense.

Plant description:

*Plant and growth habit.*—Compact and outwardly spreading to trailing growth habit. Freely branching habit with about eight lateral branches developing per plant. Moderately vigorous growth habit.

*Plant height.*—About 35 cm.

*Plant diameter.*—About 83 cm.

Lateral branch description:

*Length.*—About 41.5 cm.

*Diameter.*—About 4.8 mm.

*Internode length.*—About 2.9 cm.

*Aspect.*—Initially upright to outwardly spreading.

*Texture.*—Pubescent.

*Color.*—144A.

Foliage description:

*Arrangement.*—Before flowering, alternate, simple; after flowering, opposite, simple.

*Length.*—About 4.9 cm.

*Width.*—About 3.6 cm.

*Shape.*—Elliptic.

*Apex.*—Acute.

*Base.*—Attenuate.

*Margin.*—Entire.

*Texture, upper and lower surfaces.*—Pubescent.

*Venation pattern.*—Pinnate; arcuate.

*Color.*—Developing foliage, upper surface: 146A. Developing foliage, lower surface: 146B. Fully expanded foliage, upper surface: 147A; venation, 144B. Fully expanded foliage, lower surface: 146A; venation, 144B.

*Petiole length.*—About 5 mm.

*Petiole diameter.*—About 3 mm.

*Petiole texture, upper and lower surfaces.*—Pubescent.

*Petiole color, upper and lower surfaces.*—144A.

Flower description:

*Flower arrangement and habit.*—Double-type flowers; singly arising from leaf axils. Freely flowering habit with usually about 117 developing per plant. Flowers persistent. Flowers face mostly outwardly.

*Fragrance.*—Slightly, pleasant.

*Natural flowering season.*—Plants flower continuously during the summer in the United Kingdom. Early flowering habit, plants typically beginning flowering about seven weeks after planting.

*Flower longevity.*—Individual flowers last about four days on the plant.

*Flower diameter.*—About 7.6 cm.

*Flower throat diameter.*—About 1.9 cm.

*Flower tube length.*—About 2.6 cm.

*Flower tube diameter (base).*—About 6.1 mm.

*Flower bud.*—Shape: Ovoid. Length: About 4 cm. Diameter: About 1.2 cm. Color: 79A.

*Corolla.*—Arrangement: Five petals fused at the base and opening into a flared trumpet; five to ten petaloids, some with anthers affixed. Petaloids variable in shape and size. Petal length from throat: About 3.3 cm. Petal lobe width: About 3.6 cm. Petal shape: Spatulate. Petal apex: Emarginate. Petal margin: Entire; slightly undulate. Petal texture, upper and lower surfaces: Smooth, glabrous. Throat texture: Smooth, glabrous. Tube texture: Pubescent. Color: Petals and petaloids, when opening, upper surface: 81C; venation, 79B. Petals and petaloids, when opening, lower surface: 80B; venation towards the center, 200A; venation towards the margin, 79A. Petals and petaloids, fully opened, upper surface: 77C; color becoming closer to 76B with development; venation, 77A to darker than 77A. Petals and petaloids, fully opened, lower surface: 77B; venation, 79A. Flower throat: Close to 77A. Flower tube: 155D; venation, 79A.

*Calyx.*—Arrangement: One star-shaped calyx tube with five sepals fused at the base per flower. Sepal length: About 1.7 cm. Sepal width: About 4 mm. Sepal shape: Narrowly oblong. Sepal apex: Obtuse. Sepal margin: Entire. Sepal texture, upper and lower surfaces: Pubescent. Color, immature and mature, upper and lower surfaces: 146A.

*Peduncles.*—Length: About 4.7 cm. Diameter: About 1.8 mm. Strength: Strong. Texture: Pubescent. Color: 144A slightly overlain with 200B.

*Reproductive organs.*—Stamens: Quantity: About 16 to 20 per flower. Anther shape: Ovate. Anther length:

About 2 mm. Anther color: 115D. Pollen amount: Abundant. Pollen color: 116C. Pistils: None observed. Seed/fruit: Seed and fruit development have not been observed on plants of the new *Petunia*.

Garden performance: Plants of the new *Petunia* have been observed to have good garden performance and tolerate wind, rain and temperatures ranging from about 1° C. to about 40° C.

Pathogen/pest resistance: Plants of the new *Petunia* have not been observed to be resistant to pathogens and pests common to *Petunia*.

It is claimed:

1. A new and distinct *Petunia* plant named 'Kerprilcomp' as illustrated and described.

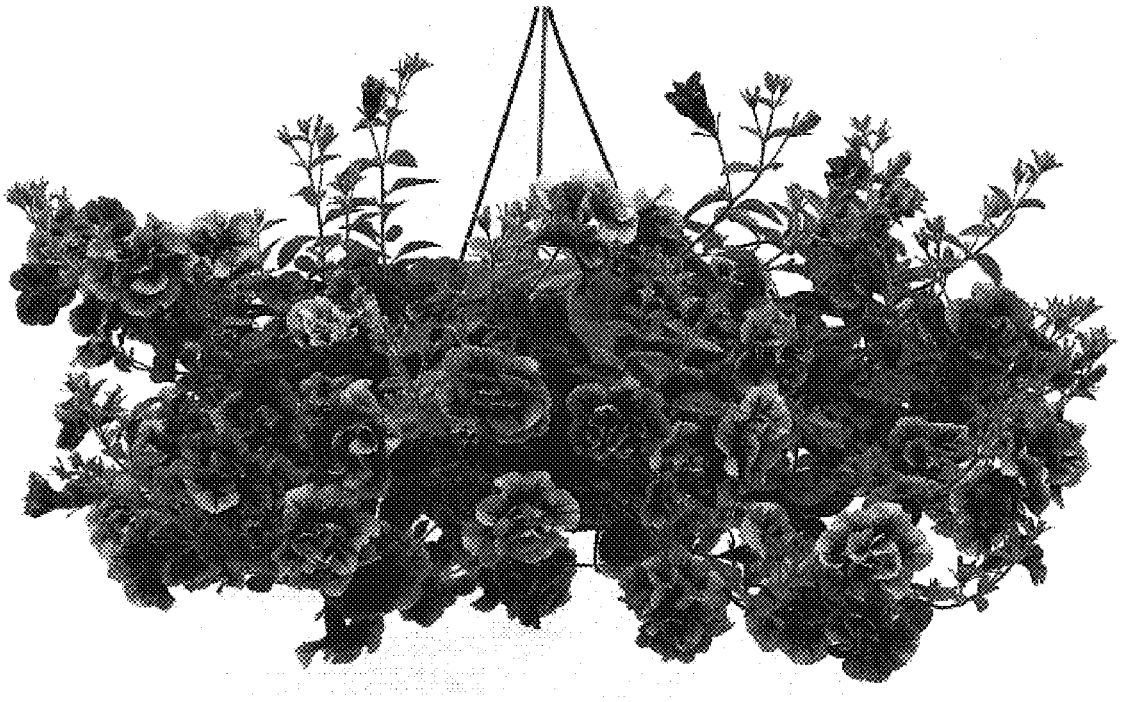

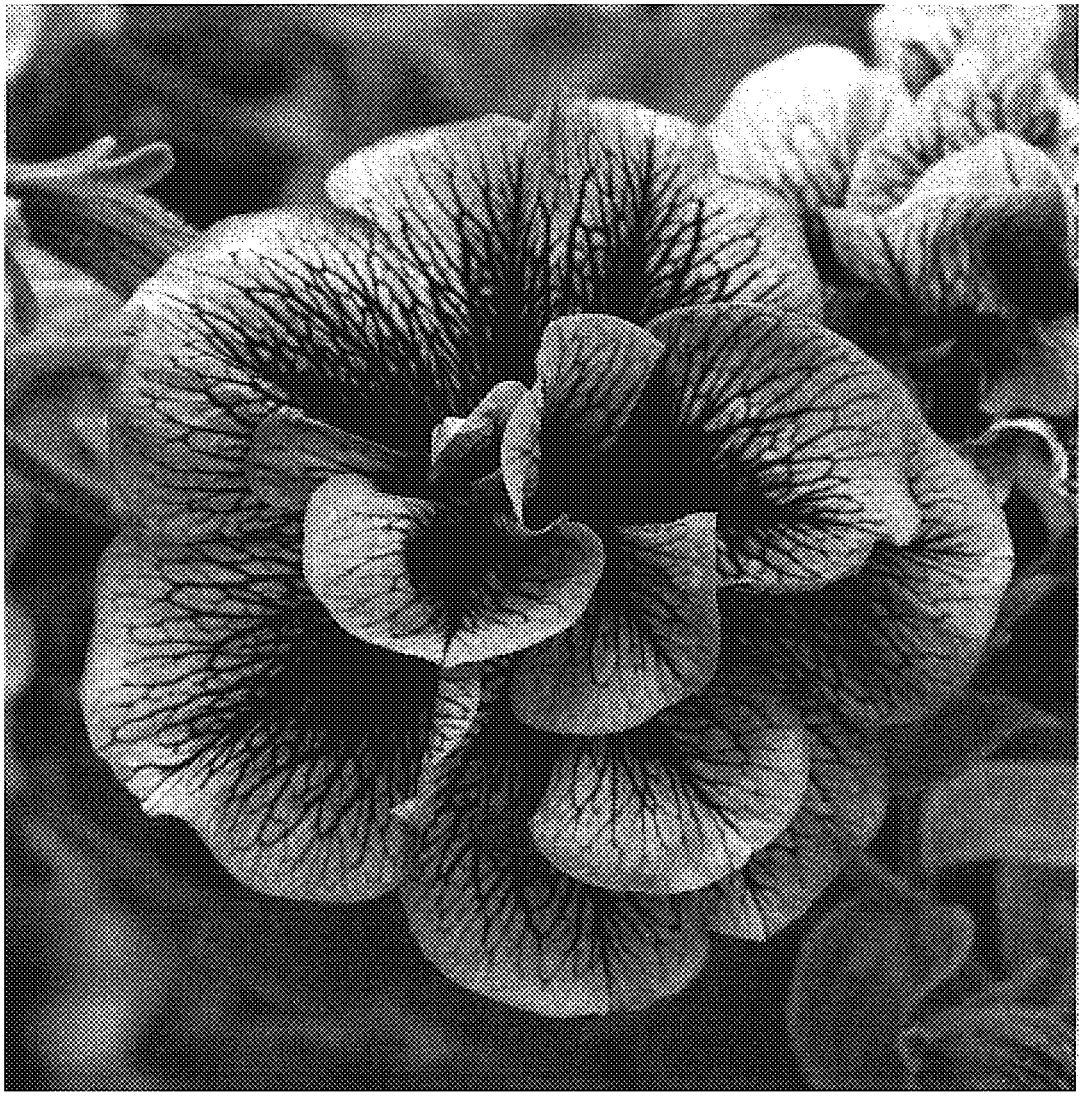

* * * * *